(12) United States Patent
Talpade

(10) Patent No.: US 6,772,000 B2
(45) Date of Patent: Aug. 3, 2004

(54) MAGNETIC RESONANCE IMAGING DEVICES WITH A CONTRAST MEDIUM FOR IMPROVED IMAGING

(75) Inventor: Dnyanesh Talpade, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 238 days.

(21) Appl. No.: 10/052,876

(22) Filed: Oct. 19, 2001

(65) Prior Publication Data

US 2003/0078492 A1 Apr. 24, 2003

(51) Int. Cl.[7] .............................................. A61B 5/055
(52) U.S. Cl. ....................... 600/420; 600/423; 600/318
(58) Field of Search ................................ 600/407, 410, 600/420, 422, 423, 424, 431, 433, 434, 435; 324/307, 309, 318, 322

(56) References Cited

U.S. PATENT DOCUMENTS

| | | | |
|---|---|---|---|
| 5,154,179 A | | 10/1992 | Ratner ..................... 128/653.4 |
| 5,411,730 A | * | 5/1995 | Kirpotin et al. ......... 424/9.322 |
| 5,928,145 A | | 7/1999 | Ocali et al. ................. 600/410 |
| 6,628,980 B2 | * | 9/2003 | Atalar et al. ................ 600/423 |

OTHER PUBLICATIONS

Volkov, Andrei, "Contrast Agents in Magnetic Resonance Imaging," Term Paper, 17 pp, May 23, 1997, Utah (Source: http://www.cc.utah.edu/~av6a51/mri.htm).
Ballinger, Ray, "Negative GI Contrast Agents", last modified Mar. 5, 1996 (Source: http://www.mritutor.org/mritutor/negcon.htm).

* cited by examiner

Primary Examiner—Eleni Mantis Mercader
(74) Attorney, Agent, or Firm—Orrick, Herrington & Sutcliffe, LLP

(57) ABSTRACT

Described herein is a medical device, such as a catheter or guidewire, which comprises an elongate body, a MRI imaging sensor and a contrast medium contained within the medical device, the contrast medium enhancing the MRI image of body tissue. The contrast medium may be contained or encapsulated in the elongate body, the imaging sensor, or a reservoir(s) in the elongate body or imaging sensor. The contrast medium may be, for example, gadolinium or a superparamagnetic contrast medium.

8 Claims, 1 Drawing Sheet

MAGNETIC RESONANCE IMAGING DEVICES WITH A CONTRAST MEDIUM FOR IMPROVED IMAGING

BACKGROUND OF THE INVENTION

1. Field of the Invention

The field of the invention is medical devices for magnetic resonance imaging ("MRI") and more specifically, medical devices having a contrast medium for enhancing MRI images of body tissues and devices.

2. Background

Medical devices are often inserted into the body of a patient. These medical devices include catheters, guidewires and other devices. After insertion of the medical device into a patient's body, medical personnel may use imaging techniques to take images of the body tissue near the medical device. For example, it may be desirable to insert a catheter having an angioplasty balloon into the body and then image the blood vessel near the balloon in order to determine the appropriate placement of the balloon relative to a partial occlusion. Alternatively, one may want to image the blood vessel after the balloon has treated the partial occlusion in order to ascertain the effectiveness of the treatment.

Commonly used medical devices are often difficult to see on MRI scans because they fail to produce sufficient contrast with respect to the surrounding body tissue or structures and/or are too small to be readily detected. Specifically, this is true for foreign objects such as catheters which are introduced into the body. U.S. Pat. No. 4,572,198 appreciated this problem and stated that if the structural portions of the catheter are simply more hydrogenous than the tissue surrounding the catheter, the catheter is detectable, but a limit is placed on the available contrast. Because of the electronic noise that they introduce to the imaging apparatus, additional functional elements such as electrode wires and the like employed in U.S. Pat. No. 4,572,198 significantly degrade the magnetic resonance image often to the point of complete image obliteration. If it is usable at all, the resulting image would be clinically less diagnostic and would make accurate localization of the implanted catheter difficult if not impossible. This appears at best to be a difficult and tenuous solution to the problem.

To improve one's ability to ascertain the position of the medical device within the body, the prior art has taken various approaches to improve the visibility of the medical device in the images taken. For instance, prior art medical devices have used materials within the devices and textures of the devices' surfaces in order to increase the "contrast" or visibility of the medical devices in images. For example, see PCT patent application WO 98/22022 by ITI Medical Technologies, Inc. and U.S. Pat. No. 5,154,179, issued on Oct. 13, 1992 to Medical Magnetics, Inc. Although prior art medical devices have used materials or textures to create "contrast," such prior art devices use the materials or textures to make the medical devices more visible during imaging. However, there is a need to improve the quality of images of the body tissue itself, and not just those of the medical device. The improved medical device explained in this patent specification satisfies that need by enhancing the quality of images of body tissues and the device. Also, there is an additional need to further improve the visibility of implanted medical devices.

SUMMARY OF THE INVENTION

The invention relates generally to a medical MRI device for insertion into a body, the device having an imaging sensor for receiving signals and a contrast medium for enhancing signals received by the imaging sensor. In an example embodiment, the improved MRI device has an imaging sensor located near the distal portion of the device and a contrast medium disposed within the body of the device and located adjacent the imaging sensor. In a second embodiment, the contrast medium of the improved MRI device is contained within a portion of the imaging sensor itself. The improved MRI device may be, for example, a catheter or guidewire. A plurality of contrast media may be used, as desired. The contrast medium enhances the quality of MRI images of the body tissue and medical devices.

A first, separate aspect of the invention is a medical device comprising an imaging sensor for receiving signals used to generate a MRI image of body tissue and a contrast medium within the medical device for enhancing signals of the body tissue received by the imaging sensor in order to generate an enhanced MRI image of the body tissue.

A second, separate aspect of the invention is a medical device comprising an antenna for receiving signals used to generate a MRI image of body tissue and a contrast medium for enhancing signals of the body tissue received by the antenna in order to generate an enhanced MRI image of the body tissue.

A third, separate aspect of the invention is a medical device comprising an imaging sensor for receiving signals used to generate a MRI image of body tissue and a contrast medium within the medical device and adjacent the imaging sensor for enhancing signals of the body tissue received by the imaging sensor in order to generate an enhanced MRI image of the body tissue.

A fourth, separate aspect of the invention is a medical device comprising an imaging sensor for receiving signals used to generate a MRI image of body tissue and a contrast medium within the medical device and adjacent the imaging sensor for enhancing signals received by the imaging sensor of the body tissue in order to generate an enhanced MRI image of the body tissue, where the contrast medium comprises gadolinium or a superparamagnetic contrast medium.

A fifth, separate aspect of the invention is a medical device comprising an imaging sensor for receiving signals used to generate a MRI image of body tissue, a reservoir in the body of the medical device, and a contrast medium contained within the reservoir for enhancing signals of the body tissue received by the imaging sensor in order to generate an enhanced MRI image of the body tissue.

A sixth, separate aspect of the invention is a medical device comprising an imaging sensor for receiving signals used to generate a MRI image of body tissue, a reservoir in the medical device, and a contrast medium contained within the reservoir for enhancing signals of the body tissue received by the imaging sensor in order to generate an enhanced MRI image of the body tissue, where the contrast medium comprises gadolinium or a superparamagnetic contrast medium.

A seventh, separate aspect of the invention is a medical device comprising an elongate body, an imaging sensor positioned on the distal portion of the elongate body, the imaging sensor receiving signals from body tissue, and a contrast medium within the imaging sensor for enhancing signals of the body tissue received by the imaging sensor in order to generate an enhanced MRI image of the body tissue.

An eighth, separate aspect of the invention is a medical device comprising an elongate body, an imaging sensor positioned on the distal portion of the elongate body, the imaging sensor receiving signals from body tissue, a reservoir, and a plurality of contrast mediums within the reservoir for enhancing signals of the body tissue received by the imaging sensor in order to generate an enhanced MRI image of the body tissue.

A ninth, separate aspect of the invention is a medical device comprising an elongate body, an imaging sensor positioned on the distal portion of the elongate body, the imaging sensor receiving signals from body tissue, a reservoir having first and second compartments, a first contrast medium contained within the first compartment, and a second contrast medium contained within the second compartment, the first and second contrast mediums enhancing signals of the body tissue received by the imaging sensor in order to generate an enhanced MRI image of the body tissue.

A tenth, separate aspect of the invention is a method of imaging body tissue from within a body comprising the steps of inserting a medical device with an imaging sensor into the body adjacent the body tissue to be imaged, positioning a contrast medium adjacent the body tissue to be imaged, and imaging the body tissue.

An eleventh, separate aspect of the invention is a method of imaging body tissue from within a body comprising the steps of introducing a selected contrast medium into a reservoir of a medical device, inserting the medical device with an imaging sensor into the body adjacent the body tissue to be imaged, positioning the reservoir of the contrast medium adjacent the body tissue to be imaged, and imaging the body tissue.

A twelfth, separate aspect of the invention is a method of imaging body tissue from within a body comprising the steps of introducing a first selected contrast medium into a first compartment of a reservoir of a medical device, introducing a second selected contrast medium into a second compartment of a reservoir of the medical device, inserting the medical device with an imaging sensor into the body adjacent the body tissue to be imaged, positioning the reservoir of the contrast medium adjacent the body tissue to be imaged, and imaging the body tissue.

A thirteenth, separate aspect of the invention is a method of imaging body tissue from within a body comprising the steps of inserting a first medical device with an imaging sensor into the body adjacent the body tissue to be imaged, introducing a second medical device adjacent the body tissue to be imaged, the second medical device containing a contrast medium for enhancing the image of the body tissue generated from signals received by the imaging sensor of the first medical device, and imaging the body tissue with the first medical device.

The invention may include any one of these separate aspects individually, or any combination of these separate aspects.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
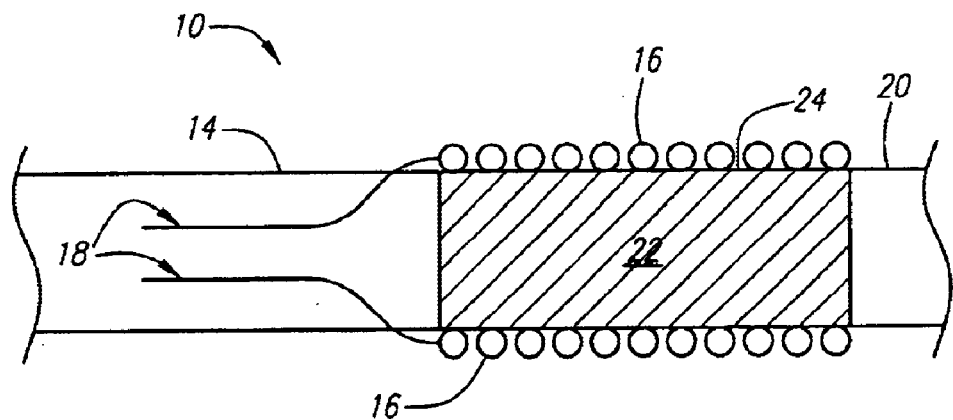
FIG. 1 is a block diagram illustrating an example embodiment of a medical device having a contrast medium for enhancing images of body tissue, where the contrast medium is contained within a reservoir of the elongate body of the medical device.

FIG. 1 is a block diagram illustrating a first example embodiment of a medical device having a contrast medium for enhancing MRI images of body tissue, where the contrast medium is contained within a reservoir of an elongate body of the medical device. The medical device 10 has an elongate body 14. The medical device 10 may be any kind or type of medical device that is inserted into the body of a patient. For example, the medical device 10 may be a catheter or guidewire. Preferably, the medical device 10 is a guidewire used for guidewire tracking within a body. An imaging sensor 16 is mounted to the device body 14. The imaging sensor 16 may be, for instance, a coil, loop, monopole antenna, dipole antenna, imaging helix, or loosely coupled profiling coil. There may be electrical leads 18 to connect the imaging sensor 16 to a power source (not shown). A contrast medium or substance 22 is provided within the device body 14 so as to isolate the contrast medium 22 from body fluids. The contrast medium 22 preferably is placed at or near the distal end portion 20 of the device body 14. In the example embodiment illustrated in FIG. 1, the contrast medium 22 is encapsulated within a reservoir 24 of the device body 14, where the reservoir 24 is sealed or closed. For example, the reservoir 24 may be a portion of the device body 14 or even the space between walls of the body 14. By encapsulating the contrast medium 22 within the reservoir 24 of the device body 14, the position of the contrast medium 22 is known and the contrast medium 22 is isolated from other portions of the medical device 10 and from other devices. For instance, there may be electrical leads 16, or other devices, in the medical device 10 which must be kept separated from the contrast medium 22.

As another embodiment, there can be two separate medical devices, one of which includes the imaging sensor 16 and the other including the reservoir 24 for containing the contrast medium 22. The two medical devices can be placed adjacent the body tissue to be imaged. The medical device containing the contrast medium 22 can act to enhance the images of the body tissue generated from signals received by the imaging sensor 16 of the other medical device. In this embodiment, the contrast medium 22 is in a medical device separate from that having the imaging sensor 16.

Figure 2:
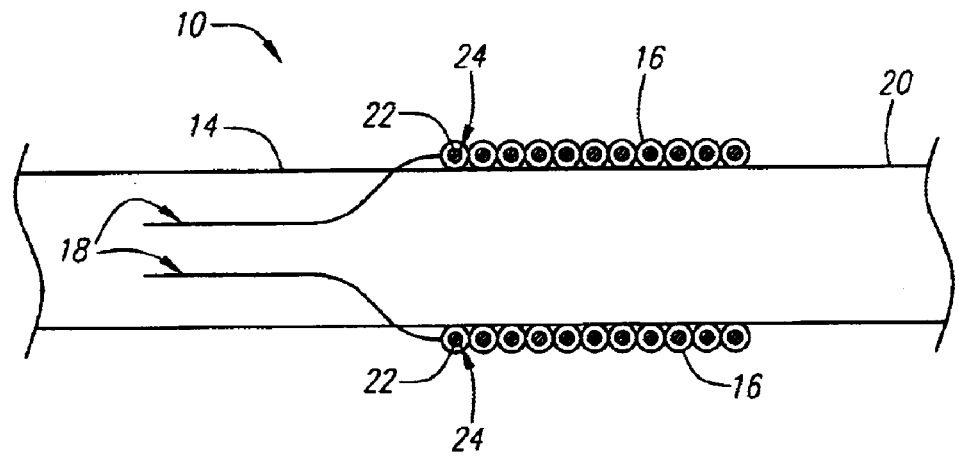
FIG. 2 is a block diagram illustrating another example embodiment of a medical device having a contrast medium for enhancing images of body tissue, where the contrast medium is contained within a reservoir in the imaging sensor.

FIG. 2 illustrates a second example embodiment of a medical device having a contrast medium for enhancing MRI images of body tissue, where the contrast medium is contained within the imaging sensor 16. Thus, instead of containing the contrast medium 22 in the elongate body 14 itself, the contrast medium 22 may be contained in a reservoir within the imaging sensor 16.

Regardless of whether the contrast medium 22 is contained within the device body 14 or the imaging sensor 16, the following observations may apply. The medical device 10 may have any number of lumens, each of which may carry instruments or other devices. Encapsulating the contrast medium 22 within the reservoir 24 prevents the contrast medium 22 from flowing out of the medical device 10 and from interacting undesirably with other devices. Of course, the reservoir 24 may be of any size and shape, as desired. The reservoir 24 can even be channels within the walls of the device body 14 or of the imaging sensor 16.

Alternatively, the contrast medium 22 can be injected through a lumen in the body 14 of the medical device 10 so as to fill the reservoir 24 within the medical device 10. This allows users to inject different kinds of contrast mediums, each of which may be better suited for a different application. After injection, the reservoir 24 can be sealed to prevent the contrast medium 22 from interacting with other devices. One possible manner of having a sealed reservoir 24 is to have a one-way valve leading to the reservoir 24, which permits the user to inject the contrast medium 22 into the reservoir 24 without worrying about leakage of the contrast medium 22 into other portions of the medical device 10 or the body.

The contrast medium 22 may be a variety of materials such as gadolinium or a superparamagnetic contrast medium. Various types of superparamagnetic contrast media or agents are well known to those of skill in the art. For example, the superparamagnetic contrast medium may essentially be ferric oxide in dextran. Some articles on the internet about the use of superparamagnetic contrast media for medical imaging include http://www.mritutor.org/mritutor/negcon.htm and "Contrast Agents in Magnetic Resonance Imaging", Andrei Volkov, May 23, 1997, at http://www.cc.utah. edu/~av6a51/mri.htm, both articles being incorporated herein by reference.

The contrast medium 22 should be selected so as to enhance the signals received by the imaging coil 16 from body tissue. Because the body tissue being imaged may differ and because the medical device 10 may be used in various parts of the body, the selected contrast medium 22 may vary from application to application. In the example of a MRI medical device, the contrast medium 22 include any material containing gadolinium or a superparamagnetic contrast medium, for instance. The material can be pure gadolinium, or some other material such as a protein bonded with gadolinium. The contrast medium 22 can be a gas, fluid, liquid, gel, or solid, as desired.

The reservoir 24 can have sections or compartments so that the contrast medium 22 can fill selected sections. Also, each section or compartment of the reservoir 24 can contain a different contrast medium. Each section can contain a contrast medium 22 or a mixture of contrast mediums 22.

The contrast medium 22 may be selected to enhance or alter the signals received by the imaging sensor 16. As a result of the enhanced signals received from the body tissue, enhanced images of the body tissue may be generated. For example, by using the contrast medium 22, medical personnel can better image areas of the body which have insufficient spin protons to generate clear images if the contrast medium 22 were not used.

While various embodiments of the application have been described, it will be apparent to those of ordinary skill in the art that many embodiments and implementations are possible that are within the scope of the invention. Therefore, the invention is not to be restricted or limited except in accordance with the following claims and their equivalents.

I claim:

1. A medical device for magnetic resonance imaging of body tissue comprising:
   an elongate body having a distal end portion and a proximal end portion, the distal end portion being adapted for insertion into a body;
   an imaging sensor disposed at or near the distal end portion of the elongate body, the imaging sensor receives signals from the body tissue for generating a magnetic resonance image of the body tissue and
   an enclosed section, having a reservoir, within the imaging sensors wherein the reservoir of the enclosed section of the imaging sensor is filled with a contrast medium whereby the contrast medium enhances signals received by the imaging sensor of the body tissue in order to generate an enhanced magnetic resonance image of the body tissue.

2. The medical device of claim 1 wherein the imaging sensor includes a coil, loop, helix, and/or a loosely coupled profiling coil.

3. The medical device of claim 1 wherein the imaging sensor includes a monopole antenna or dipole antenna.

4. The medical device of claim 1 wherein the contrast medium comprises gadolinium.

5. The medical device of claim 1 wherein the medical device comprises a catheter.

6. The medical device of claim 1 wherein the medical device comprises a guidewire.

7. The medical device of claim 1 wherein the imaging sensor comprises a plurality of sections, where each section may contain a different contrast medium.

8. The medical device of claim 1 further comprising:
   a lumen disposed within the elongate body and coupled to the enclosed section of the imaging sensor; and
   a one-way valve coupled to the enclosed section via the lumen, the valve permitting a user to inject the contrast medium into the enclosed section through the lumen.

* * * * *